United States Patent
Stanulis et al.

(10) Patent No.: US 11,401,239 B1
(45) Date of Patent: Aug. 2, 2022

(54) PROCESS FOR CONVERTING DISULFIDES TO CONVERSION PRODUCTS AND PROCESS FOR PRODUCING CYSTEIC ACID

(71) Applicant: FXI INC. LIMITED, London (GB)

(72) Inventors: Andrius Stanulis, Swansea (GB); Andrew R. Barron, Swansea (GB)

(73) Assignee: FXI INC. LIMITED, London (GB)

( * ) Notice: Subject to any disclaimer, the term of this patent is extended or adjusted under 35 U.S.C. 154(b) by 0 days.

(21) Appl. No.: 17/319,921

(22) Filed: May 13, 2021

Related U.S. Application Data

(60) Provisional application No. 63/090,739, filed on Oct. 13, 2020.

(51) Int. Cl.
C07C 303/16 (2006.01)

(52) U.S. Cl.
CPC ................................. C07C 303/16 (2013.01)

(58) Field of Classification Search
CPC .................................................. C07C 303/16
See application file for complete search history.

(56) References Cited

U.S. PATENT DOCUMENTS

| | | | |
|---|---|---|---|
| 4,053,630 A | 10/1977 | Yu et al. | |
| 4,283,386 A | 8/1981 | Van Scott et al. | |
| 4,490,529 A | 12/1984 | Rosowsky | |
| 4,496,548 A | 1/1985 | Moldowan et al. | |
| 5,059,711 A * | 10/1991 | Bielefeldt | C07C 309/00 562/113 |
| 6,849,082 B2 | 2/2005 | Azevedo | |
| 9,018,142 B2 | 4/2015 | Rovison, Jr. et al. | |
| 9,045,600 B2 | 6/2015 | Kelly et al. | |
| 9,242,876 B2 | 1/2016 | Barron et al. | |
| 9,936,785 B2 | 4/2018 | Shioda | |
| 10,138,204 B2 | 11/2018 | Babrou et al. | |
| 10,322,996 B2 | 6/2019 | Babrou et al. | |
| 2009/0209738 A1 | 8/2009 | Cranston et al. | |
| 2016/0235082 A1 | 8/2016 | Patel et al. | |

FOREIGN PATENT DOCUMENTS

| | | |
|---|---|---|
| EP | 1039873 A1 | 10/2000 |
| FR | 2529214 A1 | 12/1983 |
| JP | 2002332272 A | 11/2002 |
| JP | 2011132152 A | 7/2011 |
| NZ | 585675 A | 11/2011 |
| WO | 2014095318 A2 | 6/2014 |

OTHER PUBLICATIONS

Hirs (Determination of cysteine as cysteic acid, Determination of cysteine, Amino Acid Analysis and Related Procedures, pp. 59-62, Published 2004) (Year: 2004).*
Maguire-Boyle, et al, A new functionalization strategy for oil/water separation membranes. J. Membrane Sci., 2011, 382, 107-115.
Maguire-Boyle, et al, Alumoxane/ferroxane nanoparticles for the removal of viral pathogens: the importance of surface functionality to nanoparticle activity. Nanoscale, 2012, 4, 5627-5632.
Maguire-Boyle, et al, Superhydrophilic functionalization of microfiltration ceramic membranes enables separation of hydrocarbons from frac and produced water, Sci. Rep., 2017, 7, 12267.
Sanchez-Cano, et al, Synthesis of l-cysteic acid by indirect electrooxidation and an example of paired synthesis: L-cysteic and l-cysteine from l-cystine. Tetrahedron, 1991, 47, 877-886.
Babu, et al, A homogeneous redox catalytic process for the paired synthesis of l-cysteine and l-cysteic acid from l-cystine. Electrochimica Acta, 2011, 56, 9797-9801.
Joyard, et al, Synthesis of sulfonic acid derivatives by oxidative deprotection of thiols using tert-butyl hypochlorite. Org. Lett. 2013, 15, 2294-2297.
Tao, et al, Efficient preparation of L-cysteic acid and its esters. Amino Acids, 2004, 27, 149-151.
Simpson, Performic acid oxidation of proteins, Cold Spring Harbor Protocols, 2003, URL: http://cshprotocols.cshlp.org/content/2007/3/pdb.prot4698.abstract.
Hirs, Determination of cystine as cysteic acid, Determination of Cystine, 2004, URL: https://www.sciencedirect.com/science/article/pii/S0076687967110082.
Wang et al., Synthesis of L-Cysteine and L-Cysteic Acid by Paired Electrolysis Method, Chemistry Letters, 2004, 33(3), URL: https://www.journal.csj.jp/doi/abs/10.1246/cl.2004.332.

* cited by examiner

*Primary Examiner* — Yevgeny Valenrod
*Assistant Examiner* — Blaine G Doletski
(74) *Attorney, Agent, or Firm* — Patterson + Sheridan, LLP

(57) ABSTRACT

Embodiments of the present disclosure generally relate to processes for converting disulfides to conversion products and to processes for producing cysteic acid. In an embodiment, a process for converting cystine to a conversion product is provided. The process include introducing an organic peroxide and water to cystine to form a mixture. The process further includes reacting the mixture, under conversion conditions, to form the conversion product, wherein the conversion product comprises cysteic acid, an amount of cysteic acid in the conversion product is greater than about 90 wt % based on a total weight of the conversion product, and the conversion conditions comprise a conversion temperature from about 15° C. to about 50° C. The process further includes heating the conversion product to remove the organic peroxide.

20 Claims, 2 Drawing Sheets

PROCESS FOR CONVERTING DISULFIDES TO CONVERSION PRODUCTS AND PROCESS FOR PRODUCING CYSTEIC ACID

CROSS-REFERENCE TO RELATED APPLICATIONS

This application claims priority to U.S. Provisional Patent Application No. 63/090,739, filed Oct. 13, 2020, which is incorporated herein by reference in its entirety.

BACKGROUND

Field

Embodiments of the present disclosure generally relate to processes for converting disulfides to conversion products and to processes for producing cysteic acid.

Description of the Related Art

Cysteic acid, also known as 3-sulfo-L-alanine, is an organic compound having the formula $HO_3SCH_2CH(NH_2)CO_2H$. Cysteic acid is a nontoxic and nonallergenic physiological compound found in, e.g., platelets and leukocytes of human and animal blood. Cysteic acid has myriad applications, including pharmaceutical and water-decontamination uses. For example, cysteic acid has efficacy in treating ichthyotic conditions, body odor, hangovers, and skin disorders such as dandruff, acne, psoriasis, palmar hyperkeratosis, plantar hyperkeratosis, and disturbed keratinization. Conventional preventative and therapeutic treatments to alleviate the symptoms of skin disorders with disturbed keratinization typically involve the topical application of a solution, gel, lotion, cream, ointment, stick, powder, or spray containing cysteic acid. With respect to water-decontamination applications, cysteic acid-functionalized membranes show superior performance for oil/water separations as well as the removal of bacteria from contaminated water without significant fouling or reduction in membrane flux.

The production costs in making cysteic acid, however, is high (~$200/kg), as compared to cystine (~$30/kg) from which it is commonly synthesized. The high production costs are largely due to state-of-the-art methods of making cysteic acid. One conventional method for making cysteic acid involves the oxidation of cystine by bromine. The cost of molecular bromine, its safety, and post-synthesis work-up protocols render this method too time intensive and potentially hazardous. Another conventional method involves indirect electro oxidation from L-cystine using hydrobromic acid (HBr). On large scales, however, the in situ formation of bromine from HBr is hazardous. Other state-of-the-art methods for producing cysteic acid involve the use of chlorine-containing reagents, such as tert-butyl hypochlorite. The oxidizing agent tert-butyl hypochlorite, however, is costly and hazardous on a large scale due to its decomposition in water with subsequent generation of chlorine gas. Electrochemical methods for producing cysteic acid are also known, but are typically not practical for large-scale commercial applications. Each of these known methods are inefficient, require high amounts of oxidizing agents, are not useful for large-scale production, generate hazardous materials, and are too costly. The oxidation of cystine is not unique, however, as the oxidation of other compounds having disulfide bonds to useful materials is costly, inefficient, and potentially hazardous by known methods.

There is a need for new and improved methods for oxidizing compounds having disulfide bonds that overcome one or more of the aforementioned deficiencies.

SUMMARY

Embodiments of the present disclosure generally relate to processes for converting disulfides to conversion products and to processes for producing cysteic acid.

In an embodiment, a process for converting cystine to a conversion product is provided. The process include introducing an organic peroxide and water to cystine to form a mixture. The process further includes reacting the mixture, under conversion conditions, to form the conversion product, wherein the conversion product comprises cysteic acid, an amount of cysteic acid in the conversion product is greater than about 90 wt % based on a total weight of the conversion product, and the conversion conditions comprise a conversion temperature from about 15° C. to about 50° C. The process further includes heating the conversion product to remove the organic peroxide.

In another embodiment, a process for converting an organic disulfide to a conversion product is provided. The process includes introducing an organic peroxide to an organic disulfide to form a mixture, the organic disulfide having the formula $R^1$—S—S—$R^2$, wherein each of $R^1$ and $R^2$ are, independently, $C_1$-$C_{20}$ unsubstituted hydrocarbyl or $C_1$-$C_{20}$ substituted hydrocarbyl. The process further includes reacting the mixture, under conversion conditions, to form the conversion product, wherein the conversion product comprises a sulfonic acid, and an amount of sulfonic acid in the conversion product is greater than about 90 wt % based on a total weight of the conversion product. The process further includes removing the organic peroxide by heating the conversion product, placing the conversion product under a pressure of less than about 1 atm, or both.

In another embodiment, a process for converting an organic disulfide to a conversion product is provided. The process includes introducing an organic peroxide to an organic disulfide to form a mixture, the organic peroxide comprising performic acid, peracetic acid, or a combination thereof, the organic disulfide having the formula $R^1$—S—S—$R^2$, wherein each of $R^1$ and $R^2$ are, independently, $C_1$-$C_{20}$ unsubstituted hydrocarbyl or $C_1$-$C_{20}$ substituted hydrocarbyl. The process further includes reacting the mixture, under conversion conditions, to form the conversion product, wherein the conversion product comprises a sulfonic acid, and an amount of sulfonic acid in the conversion product is greater than about 90 wt % based on a total weight of the conversion product. The process further includes removing the organic peroxide by heating the conversion product, placing the conversion product under a pressure of less than about 1 atm, or both.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

Figures included herein illustrate various embodiments of the disclosure. It is contemplated that elements and features of one embodiment may be beneficially incorporated in other embodiments without further recitation.

DETAILED DESCRIPTION

Embodiments of the present disclosure generally relate to processes for converting disulfides to conversion products and to processes for producing cysteic acid. The inventors have found new and improved processes for converting disulfides, e.g., compounds having disulfide bond(s), to conversion products. Briefly, and in some embodiments, a compound having disulfide bond(s) is converted to conversion products, e.g., sulfonic acid(s), using an organic peroxide. Excess reagents used for the conversion reaction can be removed from the product or product mixture by, e.g., evaporation. In contrast to conventional methods of oxidizing compounds containing disulfide bonds, the processes described herein are efficient, inexpensive, can be performed on commercially-viable scales, and do not produce hazardous chemicals. For example, and in some embodiments, the processes described herein enable production of desired products (e.g., cysteic acid from cystine) in greater than 90% yield, with high conversion and high purity. Such high purity and high yield is not observed by practicing conventional methods where extensive purification is typically needed to obtain desired products from the crude reaction mixture. In addition, the processes described herein show decreased complexity and significantly reduced reaction time as a function of yield, or alternatively enable increased yield at comparable reaction times relative to conventional methods. Further, embodiments described herein are free of solvent extraction operation(s) and extensive work-up protocols, and the starting materials are free of solid support(s).

Figure 1:
FIG. 1 illustrates an example conversion reaction of an organic disulfide to a conversion product according to at least one embodiment of the present disclosure.

Processes described herein relate to the production of conversion products, e.g., sulfonic acids from organic disulfides. The processes generally include introducing an organic peroxide to an organic disulfide to form a mixture and reacting the mixture, under conversion conditions, to form one or more conversion products. FIG. 1 shows a general reaction scheme for the conversion of the organic disulfide 101 to example conversion products 103 and 104 using an oxidizing agent 102, such as an organic peroxide.

In some embodiments, the organic disulfide has the formula

wherein:
each of $R^1$ and $R^2$ are, independently, a $C_1$-$C_{100}$ unsubstituted hydrocarbyl (such as $C_1$-$C_{40}$ unsubstituted hydrocarbyl, such as $C_1$-$C_{20}$ unsubstituted hydrocarbyl, such as $C_1$-$C_{10}$ unsubstituted hydrocarbyl, such as $C_1$-$C_6$ unsubstituted hydrocarbyl), a $C_1$-$C_{100}$ substituted hydrocarbyl (such as $C_1$-$C_{40}$ substituted hydrocarbyl, such as $C_1$-$C_{20}$ substituted hydrocarbyl, such as $C_1$-$C_{10}$ substituted hydrocarbyl, such as $C_1$-$C_6$ substituted hydrocarbyl), a $C_4$-$C_{100}$ unsubstituted aryl (such as $C_4$-$C_{40}$ unsubstituted aryl, such as $C_4$-$C_{20}$ unsubstituted aryl, such as $C_4$-$C_{10}$ unsubstituted aryl), a $C_4$-$C_{100}$ substituted aryl (such as $C_4$-$C_{40}$ substituted aryl, such as $C_4$-$C_{20}$ substituted aryl, such as $C_4$-$C_{10}$), or $R^1$ and $R^2$ may join to form a saturated ring, unsaturated ring, substituted saturated ring, or substituted unsaturated ring, such as a substituted or unsubstituted $C_2$ to $C_{100}$ cyclic or polycyclic ring. Each of $R^1$ and $R^2$ can be, independently, saturated or unsaturated, substituted or unsubstituted, linear or branched, cyclic or acyclic, aromatic or non-aromatic. $R^1$ and $R^2$ can be the same or different.

In at least one embodiment, and when $R^1$ and/or $R^2$ is a substituted hydrocarbyl or a substituted aryl, at least one carbon of the substituted hydrocarbyl or the substituted aryl has been substituted with at least one heteroatom or heteroatom-containing group, such as one or more elements from Group 13-17 of the periodic table of the elements, such as halogen (F, Cl, Br, or I), O, N, Se, Te, P, As, Sb, S, B, Si, Ge, Sn, Pb, and the like, such as NR*$_2$, OR* (e.g., OH or O$_2$H), SeR*, TeR*, PR*$_2$, AsR*$_2$, SbR*$_2$, SR*, SO$_x$ (where x=2 or 3), BR*$_2$, SiR*$_3$, GeR*$_3$, SnR*$_3$, PbR*$_3$, and the like or where at least one heteroatom has been inserted within the hydrocarbyl radical or aryl radical such as one or more of halogen (Cl, Br, I, F), O, N, S, Se, Te, NR*, PR*, AsR*, SbR*, BR*, SiR*$_2$, GeR*$_2$, SnR*$_2$ PbR*$_2$, and the like, where R* is, independently, hydrogen, hydrocarbyl (e.g., $C_1$-$C_{10}$), or two or more R* may join together to form a substituted or unsubstituted completely saturated, partially unsaturated, fully unsaturated, or aromatic cyclic or polycyclic ring structure.

The organic peroxide can have the structure:

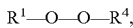

wherein:
$R^3$ is a $C_1$-$C_{40}$ unsubstituted hydrocarbyl (such as $C_1$-$C_{20}$ unsubstituted hydrocarbyl, such as $C_1$-$C_{10}$ unsubstituted hydrocarbyl, such as $C_1$-$C_6$ unsubstituted hydrocarbyl), a $C_1$-$C_{40}$ substituted hydrocarbyl (such as $C_1$-$C_{20}$ substituted hydrocarbyl, such as $C_1$-$C_{10}$ substituted hydrocarbyl, such as $C_1$-$C_6$ substituted hydrocarbyl), a $C_4$-$C_{100}$ unsubstituted aryl (such as $C_4$-$C_{40}$ unsubstituted aryl, such as $C_4$-$C_{20}$ unsubstituted aryl, such as $C_4$-$C_{10}$ unsubstituted aryl), or a $C_4$-$C_{100}$ substituted aryl (such as $C_4$-$C_{40}$ substituted aryl, such as $C_4$-$C_{20}$ substituted aryl, such as $C_4$-$C_{10}$ substituted aryl); and $R^4$ is hydrogen, a $C_1$-$C_{40}$ unsubstituted hydrocarbyl (such as $C_1$-$C_{20}$ unsubstituted hydrocarbyl, such as $C_1$-$C_{10}$ unsubstituted hydrocarbyl, such as $C_1$-$C_6$ hydrocarbyl), a $C_1$-$C_{40}$ substituted hydrocarbyl (such as $C_1$-$C_{20}$ substituted hydrocarbyl, such as $C_1$-$C_{10}$ substituted hydrocarbyl, such as $C_1$-$C_6$ substituted hydrocarbyl), a $C_4$-$C_{100}$ unsubstituted aryl (such as $C_4$-$C_{40}$ unsubstituted aryl, such as $C_4$-$C_{20}$ unsubstituted aryl, such as $C_4$-$C_{10}$ unsubstituted aryl), or a $C_4$-$C_{100}$ substituted aryl (such as $C_4$-$C_{40}$ substituted aryl, such as $C_4$-$C_{20}$ substituted aryl, such as $C_4$-$C_{10}$ substituted aryl).

In some embodiments, the organic acid is a percarboxylic acid (or peroxy acid), $R^5CO_3H$, prepared from a mixture of a carboxylic acid, $R^5CO_2H$, and hydrogen peroxide. $R^5$ can include those unsubstituted hydrocarbyls, substituted hydrocarbyls, unsubstituted aryls, and substituted aryls listed above for $R^3$ or $R^4$. In at least one embodiment, the organic peroxide is chosen such that it has an oxidation potential greater than hydrogen peroxide, e.g., greater than ~1.77 V. Each of $R^3$ and $R^4$ can be, independently, saturated or unsaturated, substituted or unsubstituted, linear or branched, cyclic or acyclic, aromatic or non-aromatic.

In some embodiments, the organic peroxide can be made from a mixture of hydrogen peroxide and an organic acid, such as a substituted or unsubstituted, branched or unbranched, cyclic or acyclic $C_1$-$C_{40}$ organic acid, $C_1$-$C_{20}$ organic acid, $C_1$-$C_{10}$ organic acid, or $C_1$-$C_6$ organic acid. Illustrative, but non-limiting, examples of organic acids include acetic acid, formic acid, benzoic acid, trifluoroacetic acid, propanoic acid, and butanoic acid. The hydrogen peroxide utilized can be in the form of an aqueous solution, such as, e.g., a ~50 wt % solution in water or less, such as a ~30 wt % solution in water or less. The organic peroxide is generated upon introduction of the organic acid to hydrogen peroxide. For example, introduction of acetic acid to hydrogen peroxide generates peracetic acid ($CH_3CO_3H$), and introduction of formic acid to hydrogen peroxide generates performic acid ($CH_2O_3$). An excess amount of the organic acid to the hydrogen peroxide, or vice-versa, can be used to generate the organic peroxide.

Useful solvents for the conversion reaction can include water and/or alcohols such as isopropanol and ethanol. Water is introduced to the organic disulfide prior to, during, and/or after the addition of the organic peroxide. In some embodiments, the organic peroxide is, or includes, an aqueous mixture having a concentration of organic peroxide of about 5% v/v or more, such as from about 10% v/v to about 80% v/v, such as from about 20% v/v to about 50% v/v, and such as from about 30% v/v to about 40% v/v.

Figure 2:
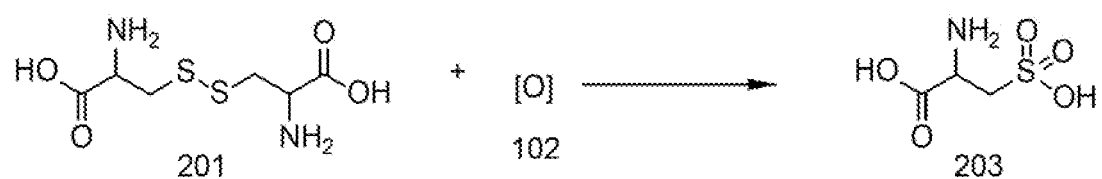
FIG. 2 illustrates an example conversion reaction of cystine to a conversion product according to at least one embodiment of the present disclosure.

As a non-limiting example of the conversion reaction described above, FIG. 2 shows the conversion of cystine to conversion products. Here, cystine ($C_6H_{12}N_2O_4S_2$) 201 is converted, under conversion conditions, to a conversion product that contains cysteic acid ($C_3H_7NO_5S$) 203. The oxidizing agent 102 ([O]) includes those organic peroxides described above.

According to some embodiments, the conversion conditions for the conversion reaction can include a temperature (e.g., a conversion temperature) and a time (e.g., a conversion time). In some embodiments, the conversion temperature is from about 0° C. to about 80° C., such as from about 5° C. to about 75° C., such as from about 10° C. to about 70° C., such as from about 15° C. to about 65° C., such as from about 20° C. to about 60° C., such as from about 25° C. to about 55° C., such as from about 30° C. to about 50° C., such as from about 35° C. to about 45° C., such as from about 40° C. to about 45° C. In at least one embodiment, the conversion temperature can be from about 15° C. to about 25° C. In some embodiments, the conversion temperature ranges from $T_1$ to $T_2$, where $T_1$ and $T_2$ (in units of ° C.) is, independently, 0, 5, 10, 15, 20, 25, 30, 35, 40, 45, 50, 55, 60, 65, 70, 75, 80, 85, 90, or 95, as long as $T_2 > T_1$. The conversion time for the conversion conditions can be at least about 1 minute (min) and/or less than about 48 hours (h), such as from about 30 min to about 10 h, such as from about 1 h to about 5 h, such as from about 2 h to about 4 h.

In some embodiments, the conversion conditions include stirring, mixing, and/or otherwise agitating the reaction mixture to ensure homogeneity of the reaction mixture. The conversion conditions can also include performing the conversion reaction under a non-reactive gas, such as $N_2$ and/or Ar. Any reasonable pressure can be used during the conversion reaction. In one embodiment, the conversion reaction is performed at or about atmospheric pressure, however, it is contemplated the conversion reaction may be performed at higher or lower pressures. In at least one embodiment, the reaction mixture is free or substantially free of halides such as bromine.

After a suitable reaction time for the conversion, the conversion product from the conversion reaction can contain one or more desired products (e.g., sulfonic acid(s)), as well as other materials such as organic acid, hydrogen peroxide, and/or organic peroxide. According to some embodiments, one or more of these materials are removed from the conversion product, under removal conditions. Removal conditions can include heating the conversion product to a temperature of about 110° C. or less, such as about 100° C. or less, such as about 90° C. or less, such as from about 30° C. to about 70° C., such as from about 40° C. to about 50° C., or from about 60° C. to about 70° C. Any reasonable pressure can be used to aid in the removal of organic acid, hydrogen peroxide, organic peroxide, and/or other materials. In one embodiment, the removal of materials is performed at or about atmospheric pressure, however, it is contemplated the material removal may be performed at higher or lower pressures. As such, excess reagents can be removed by evaporation.

In at least one embodiment, a molar ratio of the acid (e.g., the organic acid) to hydrogen peroxide in the conversion reaction is from about 3:1 to about 1:3, such as from about 2:1 to about 1:2, such as from about 1.5:1 to about 1:1.5.

In at least one embodiment, a molar ratio of organic acid to organic disulfide in the conversion reaction is from about 20:1 to about 1:1, such as from about 15:1 to about 2:1, such as from about 12:1 to about 4:1.

The conversion reaction produces a conversion product comprising a sulfonic acid (e.g., cysteic acid). The amount of sulfonic acid in the conversion product is about 75 wt % or more, such as about 80 wt % or more, such as about 85 wt % or more, such as about 90 wt % or more, such as about 95 wt % or more, such as about 99 wt % or more, such as about 100 wt %, based on a total weight of conversion product.

The percent conversion of organic disulfide to conversion product(s), such as cysteic acid, in the conversion reaction can be about 50% or more, such as about 60% or more, such as about 70% or more, such as about 75% or more, such as about 80% or more, such as about 85% or more, such as about 90% or more, such as about 95% or more, such as about 99% or more, such as about 100%, based on the amount of organic disulfide used in the conversion product.

For processes producing conversion products (e.g., sulfonic acid(s)), the molar ratio of the acid (e.g., an organic acid) to hydrogen peroxide, the molar ratio of hydrogen peroxide to organic disulfide, the molar ratio of acid to organic disulfide, and the molar ratio of organic peroxide to organic disulfide is determined based on the starting material molar ratio used for the conversion reaction.

In contrast to conventional methods of producing cysteic acid, processes described herein are, e.g., practical for large-scale commercial applications, inexpensive, and do not involve the use of, or the generation of, hazardous materials.

The following illustrative examples are not intended to limit the scope of embodiments of the present disclosure.

Examples

Figure 3:
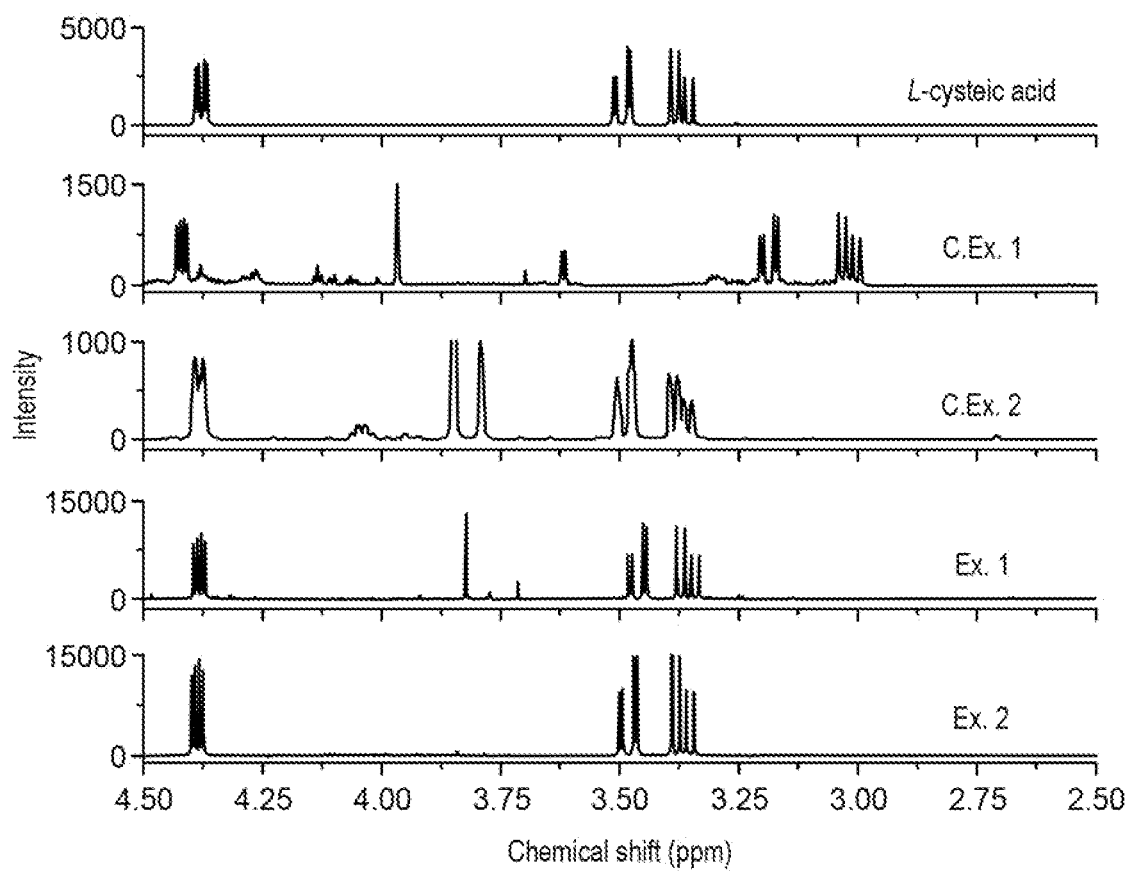
FIG. 3 shows exemplary proton nuclear magnetic resonance ($^1$H NMR) spectra of products from comparative conversion processes and example conversion processes according to at least one embodiment of the present disclosure.

Cystine, glacial acetic acid ($CH_3CO_2H$), nitric acid ($HNO_3$), formic acid ($HCO_2H$), and hydrogen peroxide solution were obtained commercially. The crude materials of the reaction product (e.g., the conversion product) for the examples and comparative examples below were analyzed by 500 MHz $^1H$ NMR, using suitable amounts of $D_2O$ as the deuterated solvent. The $^1H$ NMR spectra for the examples and comparative examples, as well as the $^1$H NMR spectrum of commercially available cysteic acid, are shown in FIG. 3.

Example 1: Cystine powder (~0.1 g) was dissolved in a mixture of glacial acetic acid (~30 mL) and ~20 mL $H_2O_2$ (30% (w/w) in $H_2O$) by stirring for 4 h at ~25° C. The excess of peracetic acid was slowly evaporated by stirring on a hot plate at about 40° C. to about 45° C. and the residue analyzed by $^1$H NMR. The $^1$H NMR spectrum of the residue is shown in FIG. 3 as Ex. 1. The yield of L-cysteic acid was >99% and the percent conversion of cystine was determined to be >99%. The results show that L-cysteic acid is produced in high purity and high yield.

Example 2: Cystine powder (0.1 g) was dissolved in a mixture of formic acid (98%, 36 mL) and about 5 mL hydrogen peroxide (30% (w/w) in $H_2O$). The mixture was stirred for about 2.5 h at about 25° C. The excess of performic acid was slowly evaporated by stirring on a hot plate at about 40° C. to about 45° C. and the residue analyzed by $^1$H NMR. The $^1$H NMR spectrum of the residue is shown in FIG. 3 as Ex. 2. The yield of L-cysteic acid was >99% and the percent conversion of cystine was determined to be >99%. The results show that L-cysteic acid is produced in high purity and high yield.

Comparative Example 1: Cystine powder (0.1 g) was added in water (10 mL). $HNO_3$ (70%, 2 mL) was added to the mixture, and the resultant mixture was stirred for 30 minutes at about 25° C. The excess water and $HNO_3$ was evaporated by stirring the mixture on a hot plate at 80° C. until dryness. The resultant powder was re-dissolved in a minimum amount of water and evaporated again. The yield of L-cysteic acid was 0% and the percent conversion of cystine was determined to be 100%. The $^1$H NMR spectrum of the residue is shown in FIG. 3 as C.Ex. 1. Here, no cysteic acid is produced as indicated by the additional peaks and broadened peaks in the $^1$H NMR spectrum.

Comparative Example 2: Cystine powder (0.1 g) was dispersed in 20 mL $H_2O_2$ (30% (w/w) in $H_2O$). The mixture was stirred for 30 minutes at 80° C. until the solution became clear. The excess water and hydrogen peroxide was evaporated by stirring on a hot plate at 80° C. The $^1$H NMR spectrum of the residue is shown in FIG. 3 as C.Ex. 2. The yield of L-cysteic acid was about 69% and the percent conversion of cystine was determined to be >98%. Here, although some cysteic acid is formed, the product residue contains substantial amounts of impurities as indicated by the additional peaks and broadened peaks in the $^1$H NMR spectrum. Furthermore, and in contrast to embodiments described herein, performing the procedures of comparative examples 1 and 2 can be challenging because, e.g., it is unsafe to maintain the temperature at 80° C. since the reaction is highly exothermic.

Overall, the results show that high-purity cysteic acid can be produced at, e.g., low temperatures, short reaction times, and complete conversion of the starting material cystine. In contrast to conventional methods of producing cysteic acid, processes described herein are practical for large-scale commercial applications, do not involve or generate hazardous materials, and are inexpensive.

Embodiments described herein enable, e.g., efficient conversion of organic disulfides to conversion products. As an example, the inventors found a new and improved process for producing cysteic acid by the reaction of cystine with an organic peroxide. The process yields high-purity cysteic acid in high yields. Moreover, removal of excess reagents can be performed by heating or placing the conversion product under reduced pressure.

In the foregoing, reference is made to embodiments of the disclosure. However, it should be understood that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the foregoing aspects, features, embodiments and advantages are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s).

As used herein, and unless otherwise specified, the term "Cn" means hydrocarbon(s) having n carbon atom(s) per molecule, wherein n is a positive integer. The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. Likewise, a "$C_m$-$C_y$" group or compound refers to a group or compound comprising carbon atoms at a total number thereof in the range from m to y. Thus, a $C_1$-$C_{50}$ alkyl group refers to an alkyl group comprising carbon atoms at a total number thereof in the range from 1 to 50.

For the purposes of this disclosure, and unless otherwise specified, the terms "hydrocarbyl radical," "hydrocarbyl group," or "hydrocarbyl" interchangeably refer to a group consisting of hydrogen and carbon atoms only. A hydrocarbyl group can be saturated or unsaturated, linear or branched, cyclic or acyclic, aromatic, or non-aromatic. For the purposes of this disclosure, and unless otherwise specified, the term "aryl" or "aryl group" interchangeably refers to a hydrocarbyl group comprising an aromatic ring structure therein.

Chemical moieties of the application can be substituted or unsubstituted unless otherwise specified. For purposes of this disclosure, and unless otherwise specified, a substituted hydrocarbyl and a substituted aryl refers to an hydrocarbyl radical and an aryl radical, respectively, in which at least one hydrogen atom has been substituted with a heteroatom or heteroatom containing group, such as with at least one functional group, such as one or more elements from Group 13-17 of the periodic table of the elements, such as halogen (F, Cl, Br, or I), O, N, Se, Te, P, As, Sb, S, B, Si, Ge, Sn, Pb, and the like, such as $NR^*_2$, $OR^*$ (e.g., OH, $O_2H$), $SeR^*$, $TeR^*$, $PR^*_2$, $AsR^*_2$, $SbR^*_2$, $SR^*$, $SO_x$ (where x=2 or 3), $BR^*_2$, $SiR^*_3$, $GeR^*_3$, $SnR^*_3$, $PbR^*_3$, and the like or where at least one heteroatom has been inserted within the hydrocarbyl radical or aryl radical such as one or more of halogen (F, Cl, Br, or I), O, S, Se, Te, $NR^*$, $PR^*$, $AsR^*$, $SbR^*$, $BR^*$, $SiR^*_2$, $GeR^*_2$, $SnR^*_2$, $PbR^*_2$, and the like, where $R^*$ is, independently, hydrogen, hydrocarbyl (e.g., $C_1$-$C_{10}$), or two or more $R^*$ may join together to form a substituted or unsubstituted completely saturated, partially unsaturated, fully unsaturated, or aromatic cyclic or polycyclic ring structure. For example, at least one hydrogen can be substituted with an oxygen-containing group such as carboxyl or carbonyl.

As another example, where isomers of a named molecule group exist (e.g., L-cysteic acid), reference to one member of the group (e.g., L-cysteic acid) shall expressly disclose the remaining isomers (e.g., R-cysteic acid) in the family. Likewise, reference to a named molecule without specifying a particular isomer (e.g., cysteic acid) expressly discloses all isomers (e.g., L-cysteic acid and R-cysteic acid).

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As used herein, the indefinite article "a" or "an" shall mean "at least one" unless specified to the contrary or the context clearly indicates otherwise. For example, aspects comprising "a monomer" include aspects comprising one, two, or more monomers, unless specified to the contrary or the context clearly indicates only one monomer is included.

While the foregoing is directed to embodiments of the present disclosure, other and further embodiments of the disclosure may be devised without departing from the basic scope thereof, and the scope thereof is determined by the claims that follow.

What is claimed is:

1. A process for converting cystine to a conversion product, comprising:
   introducing an organic peroxide and water to cystine to form a mixture;
   reacting the mixture, under conversion conditions, to form the conversion product, wherein:
   the conversion product comprises cysteic acid;
   an amount of cysteic acid in the conversion product is greater than about 90 wt % based on a total weight of the conversion product; and
   the conversion conditions comprise a conversion temperature from about 15° C. to about 50° C.; and
   heating the conversion product to remove any remaining organic peroxide.

2. The process of claim 1, wherein the amount of cysteic acid in the conversion product is greater than about 95 wt % based on the total weight of the conversion product.

3. The process of claim 1, wherein heating the conversion product to remove the organic peroxide includes heating the conversion product to a temperature of about 80° C. or less.

4. The process of claim 3, wherein the conversion temperature is from about 40° C. to about 50° C.

5. The process of claim 1, wherein a percent conversion of cystine to cysteic acid is about 95% or more.

6. The process of claim 1, wherein the organic peroxide has an oxidation potential greater than about 1.77 V.

7. The process of claim 1, wherein the organic peroxide is formed by introducing an organic acid to hydrogen peroxide.

8. The process of claim 7, wherein the organic peroxide is an aqueous solution having a concentration of organic peroxide from about 10% v/v to about 80% v/v.

9. The process of claim 1, wherein the organic peroxide comprises performic acid, peracetic acid, or a combination thereof.

10. A process for converting an organic disulfide to a conversion product, comprising:
    introducing an organic peroxide to an organic disulfide to form a mixture, the organic disulfide having the formula $R^1$—S—S—$R^2$, wherein each of $R^1$ and $R^2$ are, independently, $C_1$-$C_{20}$ unsubstituted hydrocarbyl or $C_1$-$C_{20}$ substituted hydrocarbyl;
    reacting the mixture, under conversion conditions, to form the conversion product, wherein:
    the conversion product comprises a sulfonic acid; and
    an amount of sulfonic acid in the conversion product is greater than about 90 wt % based on a total weight of the conversion product; and
    removing the organic peroxide by heating the conversion product, placing the conversion product under a pressure of less than about 1 atm, or both.

11. The process of claim 10, wherein the conversion conditions comprise a temperature from about 0° C. to about 80° C.

12. The process of claim 10, wherein the conversion conditions comprise a time of about 10 h or less.

13. The process of claim 10, wherein $R^1$ and $R^2$ are the same.

14. The process of claim 10, wherein the amount of sulfonic acid in the conversion product is greater than about 95 wt % based on the total weight of the conversion product.

15. The process of claim 10, wherein removing the organic peroxide by heating the conversion product comprises heating the conversion product to a temperature of about 80° C. or less.

16. A process for converting an organic disulfide to a conversion product, comprising:
    introducing an organic peroxide to an organic disulfide to form a mixture, the organic peroxide comprising performic acid, peracetic acid, or a combination thereof, the organic disulfide having the formula $R^1$—S—S—$R^2$, wherein each of $R^1$ and $R^2$ are, independently, $C_1$-$C_{20}$ unsubstituted hydrocarbyl or $C_1$-$C_{20}$ substituted hydrocarbyl;
    reacting the mixture, under conversion conditions, to form the conversion product, wherein:
    the conversion product comprises a sulfonic acid; and
    an amount of sulfonic acid in the conversion product is greater than about 90 wt % based on a total weight of the conversion product; and
    removing the organic peroxide by heating the conversion product, placing the conversion product under a pressure of less than about 1 atm, or both.

17. The process of claim 16, wherein the conversion conditions comprise a conversion temperature from about 15° C. to about 50° C.

18. The process of claim 16, wherein removing the organic peroxide by heating the conversion product comprises heating the conversion product to a temperature of between about 40° C. and about 50° C.

19. The process of claim 16, wherein $R^1$ and $R^2$ are the same.

20. The process of claim 16, wherein the amount of sulfonic acid in the conversion product is greater than about 95 wt % based on the total weight of the conversion product.

* * * * *